(12) United States Patent
Jaffrey

(10) Patent No.: US 10,287,869 B2
(45) Date of Patent: May 14, 2019

(54) FLUID MONITORING SYSTEMS AND METHODS

(71) Applicant: Cameron International Corporation, Houston, TX (US)

(72) Inventor: Andrew Jaffrey, Oldmeldrum (GB)

(73) Assignee: Cameron International Corporation, Houston, TX (US)

( * ) Notice: Subject to any disclaimer, the term of this patent is extended or adjusted under 35 U.S.C. 154(b) by 0 days.

(21) Appl. No.: 15/006,964

(22) Filed: Jan. 26, 2016

(65) Prior Publication Data

US 2016/0215608 A1 Jul. 28, 2016

Related U.S. Application Data

(60) Provisional application No. 62/108,521, filed on Jan. 27, 2015.

(51) Int. Cl.
*E21B 47/00* (2012.01)
*E21B 33/064* (2006.01)
*E21B 33/06* (2006.01)
*E21B 41/00* (2006.01)
*E21B 47/10* (2012.01)

(52) U.S. Cl.
CPC .............. *E21B 47/00* (2013.01); *E21B 33/06* (2013.01); *E21B 33/061* (2013.01); *E21B 33/064* (2013.01); *E21B 41/0007* (2013.01); *E21B 47/10* (2013.01)

(58) Field of Classification Search
CPC ...... E21B 47/00; E21B 47/10; E21B 41/0007; E21B 33/06; E21B 33/061; E21B 33/064
USPC ........................................................ 166/336
See application file for complete search history.

(56) References Cited

U.S. PATENT DOCUMENTS

| 8,978,699 B2 | 3/2015 | Jaffrey et al. |
| 9,677,573 B2 | 6/2017 | Jaffrey |
| 2010/0059221 A1* | 3/2010 | Vannuffelen ............ E21B 41/04 166/264 |
| 2011/0040501 A1 | 2/2011 | Martin et al. |

(Continued)

FOREIGN PATENT DOCUMENTS

WO 2014/105015 A1 7/2014

OTHER PUBLICATIONS

PCT International Search Report and Written Opinion; Application No. PCT/US2016/015194; dated Apr. 8, 2016; 13 pages.

(Continued)

*Primary Examiner* — Anna M Momper
*Assistant Examiner* — Patrick F Lambe
(74) *Attorney, Agent, or Firm* — Helene Raybaud

(57) ABSTRACT

A monitoring system includes a subsea laboratory configured to be positioned and operated below a sea surface. The subsea laboratory includes a housing, a fluid chamber within the housing and configured to receive a fluid from subsea drilling or production equipment, and a sensor within the housing and configured to generate a signal indicative of a characteristic of the fluid. The monitoring system also includes a controller having a processor configured to receive and to process the signal to determine the characteristic of the fluid, to determine an appropriate output based on the characteristic of the fluid, and to provide a control signal that causes an indication of the output via a user interface of a remote base station positioned above the sea surface.

26 Claims, 9 Drawing Sheets

(56) References Cited

U.S. PATENT DOCUMENTS

| | | | |
|---|---|---|---|
| 2012/0197527 A1* | 8/2012 | McKay | E21B 41/0007 |
| | | | 702/6 |
| 2013/0126180 A1 | 5/2013 | Phillips et al. | |
| 2014/0064029 A1 | 3/2014 | Jaffrey | |
| 2014/0123746 A1 | 5/2014 | Jaffrey et al. | |
| 2014/0231075 A1 | 8/2014 | Springett et al. | |
| 2015/0361742 A1* | 12/2015 | Gottlieb | E21B 47/0001 |
| | | | 175/48 |
| 2016/0131692 A1 | 5/2016 | Jeffrey | |
| 2016/0186516 A1 | 6/2016 | Jeffrey | |

OTHER PUBLICATIONS

U.S. Appl. No. 14/181,185, filed Feb. 14, 2014, Andrew Jaffrey.
U.S. Appl. No. 14/539,749, filed Nov. 12, 2014, Andrew Jaffrey.
U.S. Appl. No. 14/586,643, filed Dec. 30, 2014, Andrew Jaffrey.
U.S. Appl. No. 15/154,748, filed May 13, 2016, Andrew Jaffrey.
U.S. Appl. No. 15/270,261, filed Sep. 20, 2016, Hans Paul Hopper.
U.S. Appl. No. 15/419,681, filed Jan. 30, 2017, Hans Paul Hopper.

\* cited by examiner

FLUID MONITORING SYSTEMS AND METHODS

CROSS-REFERENCE TO RELATED APPLICATION

This application claims benefit of U.S. Provisional Patent Application No. 62/108,521, filed Jan. 27, 2015, entitled "INTEGRITY MANAGEMENT SYSTEM," which is incorporated by reference herein in its entirety.

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

To meet consumer and industrial demand for natural resources, exploration and production (E&P) companies often expend significant amounts of time and money finding and extracting oil, natural gas, and other subterranean resources from the earth. Particularly, E&P companies, once the resource is located, often employ drilling and production systems to access and extract the resource. These systems may be located onshore or offshore depending on the location of a desired resource.

E&P companies place a high priority on the operation and reliability of these systems, as do the supporting service providers and equipment manufacturers. Downtime due to system malfunction and maintenance can be quite costly, both in terms of actual costs and opportunity costs.

DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not require any particular orientation of the components.

Figure 1:
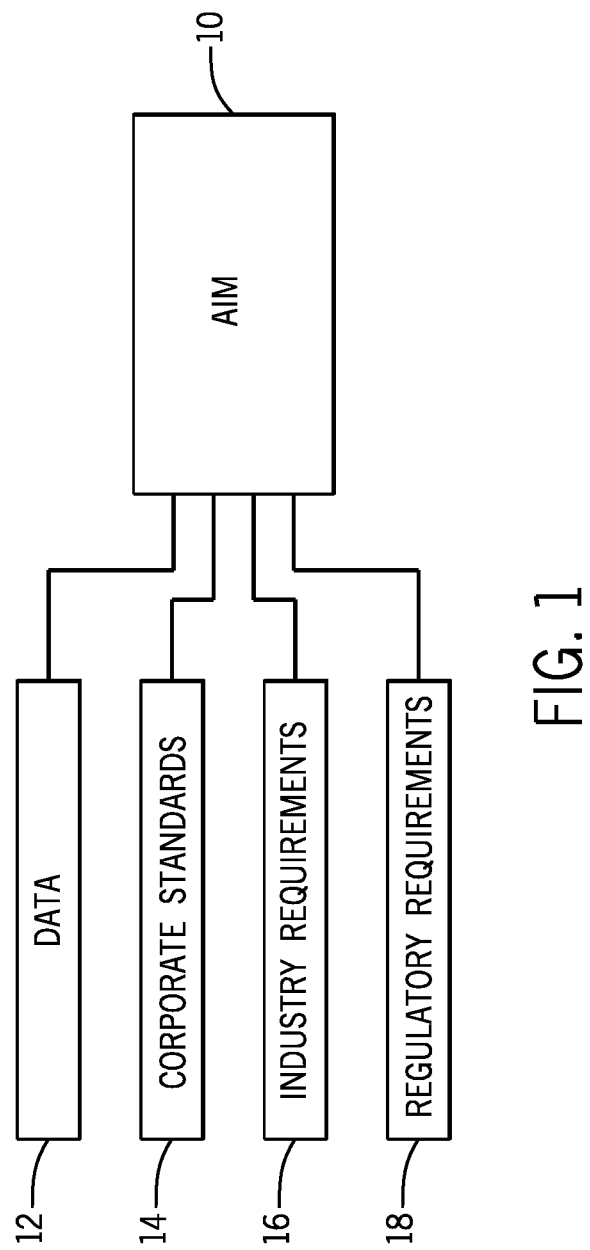
FIG. 1 describes various aspects of asset integrity management systems, in accordance with an embodiment of the present disclosure.

Turning now to the present figures, FIG. 1 describes various aspects of an asset integrity management process and system (AIM) 10. In one embodiment, the AIM 10 provides a holistic approach that facilitates a component performing its designed function effectively and efficiently within the system while also helping to mitigate health, safety, and environmental concerns by, among other things, looking at the component itself and the impact other components have on it. The AIM 10 gathers a large variety of data 12 about the drilling and production systems and correlates and complements them with corporate quality and design standards 14, industry requirements 16, and regulatory requirements 18.

The AIM 10 may be used to design, develop, build, verify, test, analyze, validate, deliver, operate, monitor, and/or maintain a component, such as a component of the drilling and production systems. For example, the AIM 10 may be used to monitor a condition of a component for predictive maintenance, which advantageously may reduce downtime, extend the life of the component, and/or reduce costs. One specific AIM-related system is Cameron International Corporation's condition-based monitoring system intended to be known as COGNITION™. Aspects of the COGNITION™ system are described in U.S. patent application Ser. Nos. 13/671,777; 13/596,759; 13/606,363; 14/181,185; 14/586,643; 14/539,749; all of which list Dr. Andrew Jaffrey as an inventor and all of which are hereby incorporated by reference in their entirety.

Because the described AIM process is holistic, the AIM 10 looks to various components of the drilling and production system to determine the source of the changed operation and the solution to it. For example, a change in performance of a component of a blowout preventer (BOP) may be a function of BOP control fluid. Thus, as discussed in more detail below, it may be desirable to monitor a characteristic of the BOP control fluid to monitor (i.e., indirectly) the component of the BOP, to determine the condition of the component of the BOP, estimate remaining life of the component, determine appropriate actions (e.g., remedial or corrective actions), and/or to predict maintenance requirements for the component of the BOP.

To facilitate discussion, certain embodiments described herein relate to monitoring hydraulic fluid or BOP control fluid; however, it should be understood that the systems and methods disclosed herein may be adapted to monitor various fluids, such as any type of supplied fluids, injected fluids, steam, gases, or the like, in any type of subsea equipment, such as subsea fluid-handling processing and production equipment. The systems and methods may be adapted to monitor a characteristic of the fluid to monitor (i.e., indirectly) a component (e.g., valves, pressure regulators, hanger, wellhead, conduits, or the like) of the subsea equipment, to determine the condition of the component, estimate remaining life of the component, determine appropriate actions (e.g., remedial or corrective actions), and/or to predict maintenance requirements for the component.

Figure 2:
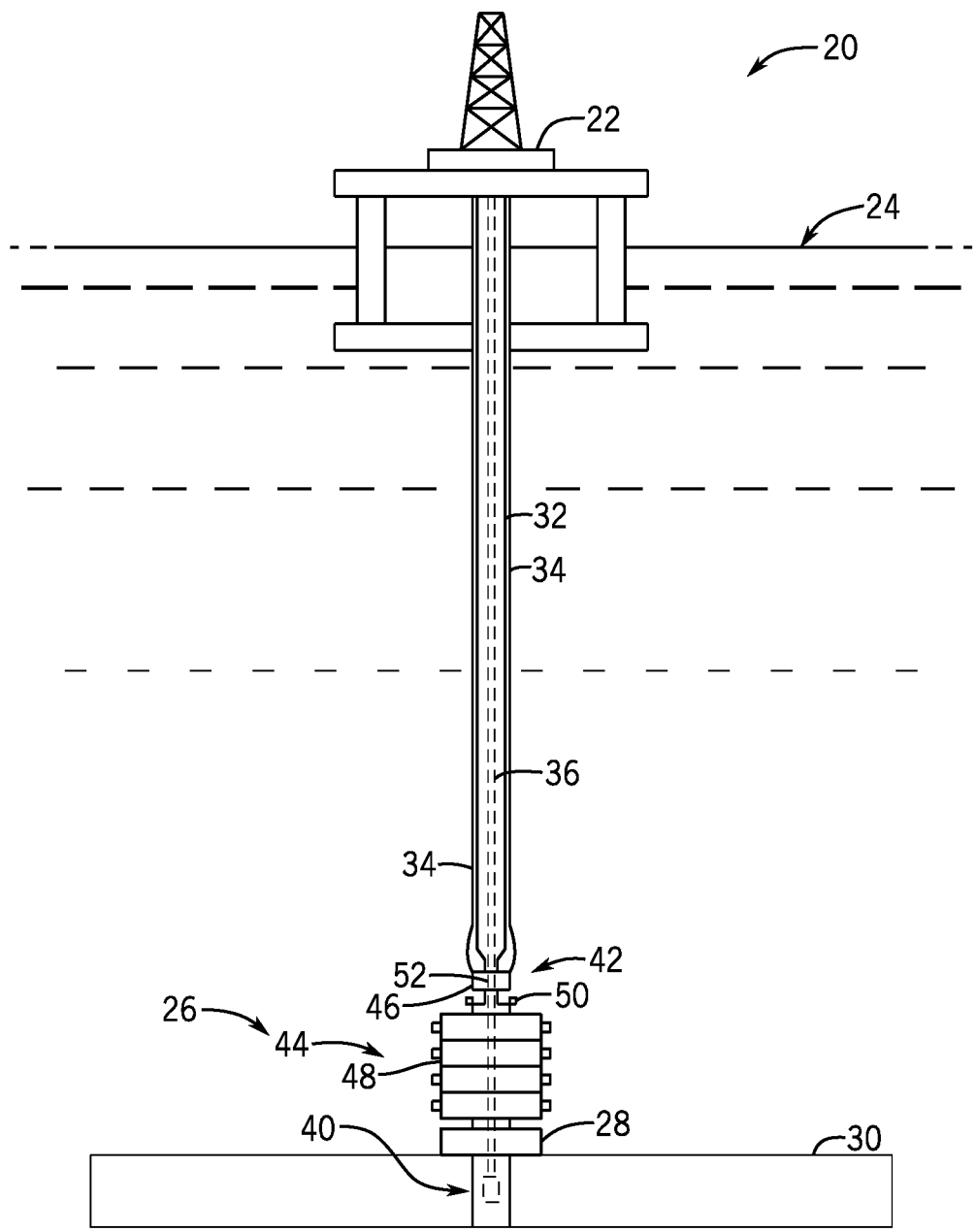
FIG. 2 is a schematic diagram of an offshore system, in accordance with an embodiment of the present disclosure.

With the foregoing in mind, FIG. 2 is a schematic diagram of an embodiment of an offshore system 20. The offshore system 20 includes an offshore vessel or platform 22 at a sea surface 24. A BOP stack assembly 26 is mounted to a wellhead 28 at a sea floor 30. A tubular drilling riser 32 extends from the platform 22 to the BOP stack assembly 26. The riser 32 may return drilling fluid or mud to the platform 22 during drilling operations. One or more conduits 34 configured to support pressurized hydraulic fluid (e.g., BOP control fluid) extend along the outside of the riser 32 from the platform 22 to the BOP stack assembly 26. Downhole operations are carried out by a tubular string 36 (e.g., drill string, production tubing string, or the like) that extends from the platform 22, through the riser 32, through the BOP stack assembly 26, and into a wellbore 40.

The BOP stack assembly 26 is configured to control and seal the wellbore 40, thereby containing hydrocarbon fluids (liquids and gases) therein. In the illustrated embodiment, the BOP stack assembly 26 includes a lower marine riser package (LMRP) 42 and a BOP stack 44. As shown, the LMRP 42 is positioned between (e.g., removably coupled to) the riser 32 and the BOP stack 44, and the BOP stack 44 is positioned between (e.g., removably coupled to) the LMRP 42 and the wellhead 28. The BOP stack assembly 26 may include one or more annular BOPs 46, one or more ram BOPs 48, one or more control units 50 (e.g., control pods), or any combination thereof.

Each annular BOP 46 includes an annular elastomeric sealing component that is mechanically squeezed radially inward via the hydraulic fluid to seal about the tubular string 36 and/or to block a flow through an annular bore 52 about the tubular string 36. Each ram BOP 48 includes a pair of opposed rams and a pair of actuators (e.g., hydraulic actuators) configured to actuate and drive the corresponding rams via the hydraulic fluid. In the illustrated embodiment, the BOP stack 44 includes four ram BOPs 48. In particular, the BOP stack 44 includes an upper ram BOP 48 that includes opposed blind shear rams or blades configured to sever the tubular string 36 and/or to seal the wellbore 40 from the riser 32 and three lower ram BOPs 48 each having opposed pipe rams configured to contact the tubular string 36 and/or to block the flow through the annular bore 52 about the tubular string 36. As discussed in more detail below, each control unit 50 may include a controller (e.g., an electronic controller having a processor, memory, and instructions) configured to control various components (e.g., valves, rams, actuators, or the like) of the BOP stack assembly 26. For example, each control unit 50 may be configured to control one or more valves to adjust a flow of hydraulic fluid (e.g., the hydraulic fluid from the conduits 34) through the BOP stack assembly 26, such as to drive the annular BOP 46 and/or the ram BOP 48 between an open position which enables fluid flow through the annular bore 52 and a closed position which blocks fluid flow through the annular bore 52.

In the illustrated embodiment, an annular BOP 46 and multiple control units 50 (e.g., redundant control units) are provided in the LMRP 42, and multiple ram BOPs 48 are provided in the BOP stack 44. It should be understood that the BOP stack 44 may include different types of ram BOPs, a different number of ram BOPs, one or more annular BOPs, one or more control units, or combinations thereof, in any suitable arrangement.

As noted above, characteristics of the hydraulic fluid may affect a condition of components (e.g., valves, conduits, BOPs, or other components having fluid-contacting surfaces) of the offshore system 20. For example, if the hydraulic fluid includes debris or particles (e.g., atypical or unacceptable size or concentration of debris or particles), the hydraulic fluid may wear or degrade surfaces of components of the offshore system 20 over time. By way of another example, the hydraulic fluid may include a biocide to deter and/or to control growth of microorganisms within the hydraulic fluid. The biocide may degrade and produce a product, such as formaldehyde, over time. Thus, if a concentration of formaldehyde in the hydraulic fluid exceeds a threshold, the hydraulic fluid may include or enable growth of microorganisms that may wear or degrade surfaces of components of the offshore system 20 over time. Accordingly, it may be desirable to monitor a characteristic of the hydraulic fluid to facilitate predictive maintenance methods for the offshore system 20.

Figure 3:
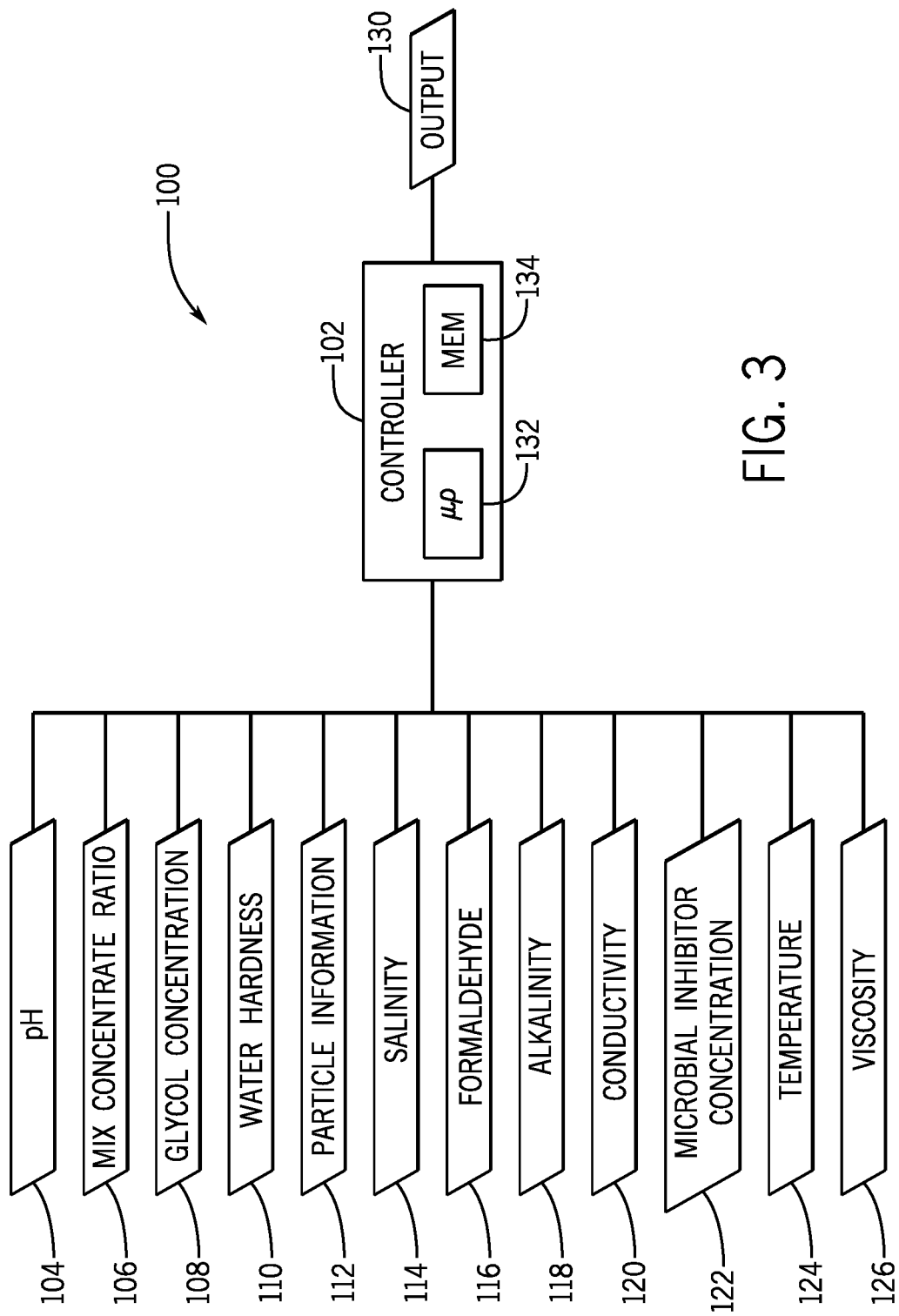
FIG. 3 is a block diagram of a monitoring system that may be utilized within the offshore system of FIG. 2, in accordance with an embodiment of the present disclosure.

FIG. 3 is a schematic diagram of a condition-based monitoring system 100 (e.g., an AIM-based system) that may be used to monitor one or more characteristics of the hydraulic fluid, and thereby monitor and/or determine a condition of components of the offshore system 20. As shown in FIG. 3, the monitoring system 100 may include a controller 102 (e.g., electronic controller). The controller 102 is configured to receive signals (e.g., inputs) indicative of characteristics of the hydraulic fluid. The controller 102 may be configured to receive signals indicative of a chemical composition of the hydraulic fluid or signals indicative of various particles or sediment within the hydraulic fluid. For example, the controller 102 may receive a signal 104 indicative of the pH of the hydraulic fluid, a signal 106 indicative of the mix concentrate ratio of the hydraulic fluid, a signal 108 indicative of the glycol concentration of the hydraulic fluid, a signal 110 indicative of the water hardness of the hydraulic fluid, a signal 112 indicative of particles (e.g., count, size, concentration, material, etc.) present in the hydraulic fluid, a signal 114 indicative of the salinity of the hydraulic fluid, a signal 116 indicative of a particular inorganic or organic compound (e.g., formaldehyde) present in the hydraulic fluid, a signal 118 indicative of the alkalinity of the hydraulic fluid, a signal 120 indicative of the conductivity of the hydraulic fluid, a signal 122 indicative of the microbial inhibitor concentration of the hydraulic fluid, a signal 124 indicative of the temperature of the hydraulic fluid, a signal 126 indicative of the viscosity of the hydraulic fluid, or any combination thereof.

The controller 102 may be configured to process signals, such as signals 104-126, to determine a characteristic of the hydraulic fluid, determine an estimated remaining life of various components, and/or to determine an appropriate action based on the characteristic of the hydraulic fluid (e.g., for predictive maintenance). In certain embodiments, the controller 102 may be configured to determine and/or to compare characteristics of the hydraulic fluid at two different locations of the offshore system 20. For example, the controller 102 may use sensors 158 to monitor the hydraulic fluid at a first location, such as a location above the sea surface (e.g., at the platform 22) prior to flowing the fluid into the conduits 34 toward the BOP stack assembly 26. The controller 102 may also use sensors 158 to monitor the hydraulic fluid extracted from a second location, such as a subsea location along the conduit 34 or within the BOP stack assembly 26. The controller 102 may compare the characteristics, which may provide an indication of affected valves, a location of a leak, broken seal, or other information about the offshore system 20.

In certain embodiments, the controller 102 may provide an output 130 based on signals, such as signals 104-126, the characteristics, and/or the comparison of characteristics. For example, the controller 102 may be configured to provide an indication (e.g., visual and/or audible indication, such as a graph or numerical value) of a characteristic of the hydraulic fluid (e.g., the pH, the mix concentrate ratio, the glycol concentration, the water hardness, particle information, salinity, formaldehyde concentration, alkalinity, conductivity, microbial inhibitor concentration, temperature, viscosity, or any combination thereof) via a display or a speaker. In some embodiments, the controller 102 may be configured to provide (e.g., via a display or a speaker) an alarm and/or a prompt, such as an estimated remaining life of a particular component, a suggestion that the hydraulic fluid be flushed through the offshore system 20, that water, certain chemical and/or additives (e.g., biocide) be added to the hydraulic fluid, or the like. In some embodiments, the controller 102 may be configured to determine and/or to provide an indication of a health score, a remaining life score (e.g., percentage remaining, years remaining, or the like) and/or a maintenance schedule (e.g., approximate date) for one or multiple components of the offshore system 20. In certain embodiments the controller 102 may be configured to monitor trends (e.g., historical data or trends in the characteristics over time, such as a period of more than about 1 hour, 12 hours, 24 hours, 48 hours, 10 days, 30 days, 60 days, 6 months, or 1 year) to determine the appropriate output 130. The controller 102 may be configured to update the indication over time based on the trends and/or current data. In certain embodiments, the controller 102 may be configured to output a control signal to automatically adjust a composition or characteristic of the hydraulic fluid (e.g., automatically control a valve to flow water, a chemical, and/or an additive, such as biocide, into the hydraulic fluid) and/or to the flush the hydraulic fluid through the offshore system 20 based on signals, such as signals 104-126, the characteristics, and/or the comparison of characteristics. Thus, the controller 102 may be configured to control actions to improve the health (e.g., operational effectiveness and/or efficiency) and/or the remaining life of the component.

As discussed in more detail below, the controller 102 may be located at the platform 22, the BOP stack assembly 26, or other suitable location of the offshore system 20, such as a remote base station (e.g., at the platform 22 or other topside location) or a laboratory (e.g., subsea laboratory or analysis station). The controller 102 may receive signals, such as the signals 104-126, via one or more sensors, which may be positioned about the BOP stack assembly 26, about the conduits 34 extending along the riser 32, and/or within a laboratory positioned subsea (e.g., at or proximate to the BOP stack assembly 26) or topside (e.g., at the platform 22). In certain embodiments, the controller 102 may include a distributed controller or control system with one or more controllers (e.g., electronic controllers with processors, memory, and instructions) distributed about the offshore system 20 and in communication with one another to receive and/or to process the signals, such as the signals 104-126, and/or to provide the output 130. For example, as discussed in more detail below, the monitoring system 100 may include one controller positioned in a subsea laboratory that is configured to receive and to process the signals 104-126 and another controller positioned in a remote or topside base station that is configured to determine and/or to provide the appropriate output 130 (e.g., on a display for visualization by an operator). In some embodiments, the monitoring system 100 may be configured to provide signals to an external system (i.e., separate from the monitoring system 100), such as the COGNITION™ system, which may include a processor configured to aggregate data or signals from multiple different monitoring systems and to provide an appropriate output (e.g., visual or audible output, such as an alarm or warning, via a user interface separate from the monitoring system 100) based on the received signals.

In certain embodiments, the controller 102 is an electronic controller having electrical circuitry configured to process signals, such as signals 104-126. In the illustrated embodiment, the controller 100 includes a processor, such as the illustrated microprocessor 132, and a memory device 134. The controller 102 may also include one or more storage devices and/or other suitable components. The processor 132 may be used to execute instructions or software. Moreover, the processor 132 may include multiple microprocessors, one or more "general-purpose" microprocessors, one or more special-purpose microprocessors, and/or one or more application specific integrated circuits (ASICS), or some combination thereof. For example, the processor 132 may include one or more reduced instruction set (RISC) processors.

The memory device 134 may include a volatile memory, such as random access memory (RAM), and/or a nonvolatile memory, such as ROM. The memory device 134 may store a variety of information and may be used for various purposes. For example, the memory device 134 may store processor-executable instructions (e.g., firmware or software) for the processor 132 to execute, such as instructions for processing the signals 104-126 to determine characteristics of the hydraulic fluid. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., characteristics of the hydraulic fluid, thresholds, etc.), instructions (e.g., software or firmware for processing the signals, etc.), and any other suitable data. The controllers, processors, and memory devices disclosed herein may have any of the above-described features.

Figure 4:
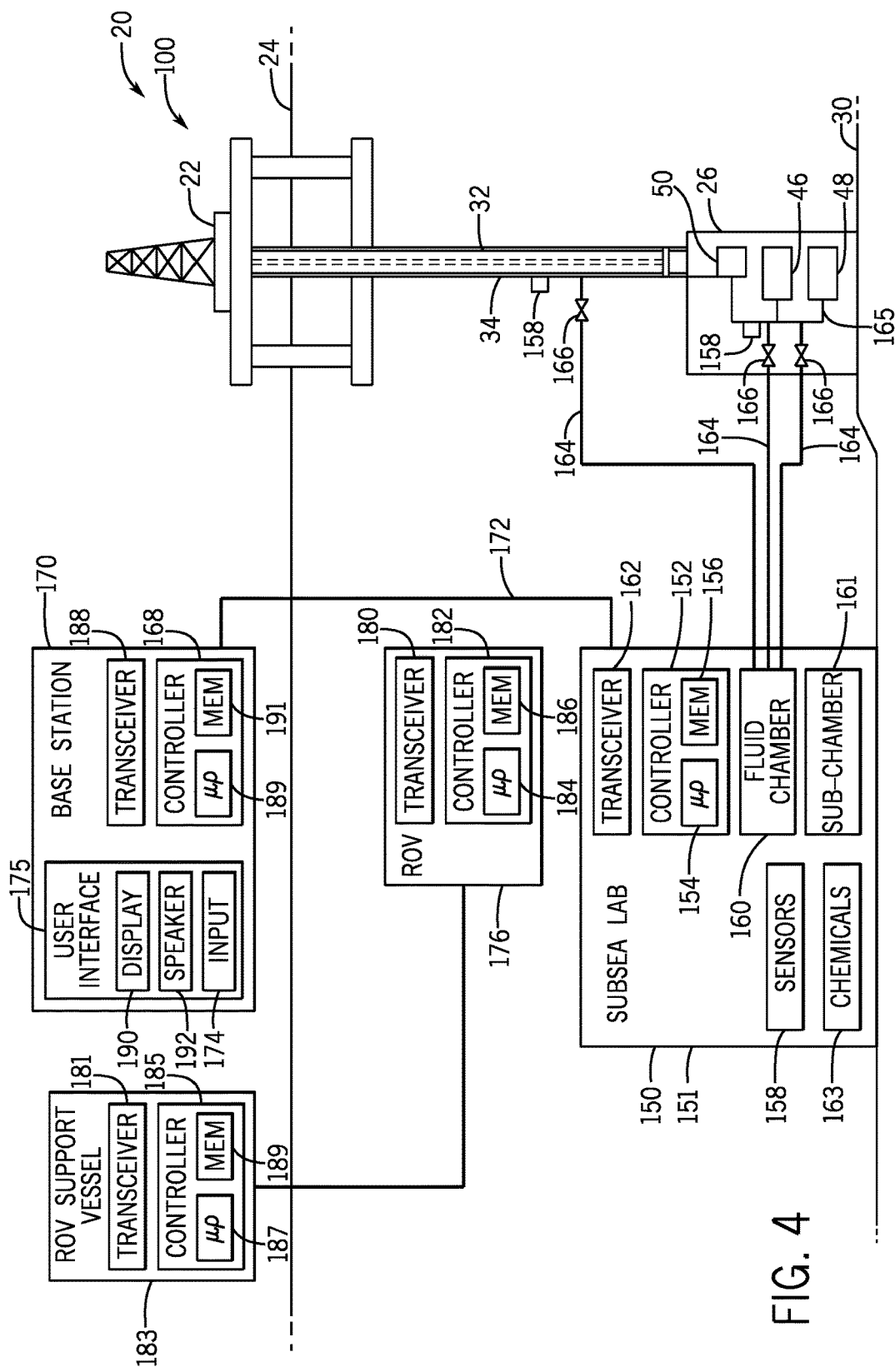
FIG. 4 is a block diagram of the monitoring system of FIG. 3 with a subsea laboratory, in accordance with an embodiment of the present disclosure.

With the foregoing in mind, the monitoring system 100 may have any of a variety of configurations to facilitate monitoring the hydraulic fluid and carrying out predictive maintenance techniques. Certain examples of possible configurations are provided in FIG. 4-7 to facilitate discussion; however, it should be understood that the sensors, controllers, user interface, and other components of the monitoring system 100 may have any of a variety of arrangements and certain features disclosed herein with respect to the examples may be combined. FIG. 4 illustrates an embodiment of the monitoring system 100 having a subsea laboratory 150 (e.g., subsea analysis station) that is configured to be positioned subsea (e.g., beneath the sea surface 24 and/or proximate to the sea floor 30). In some embodiments, the subsea laboratory 150 may contact and be supported by the sea floor 30. In some embodiments, components of the subsea laboratory 150 may be supported by a frame or a housing 151 (e.g., support member) that is coupled to (e.g., removably coupled to, fixedly attached to, or integrated within) the BOP stack assembly 26, the riser 32, and/or the conduit 34. In certain embodiments, the subsea laboratory 150 may be a freestanding or separate component (e.g., the housing 151 does not directly contact or is physically separated from the BOP stack assembly 26).

The housing 151 of the subsea laboratory 150 may be configured to withstand subsea water pressure (e.g., at depths of more than 300, 1000, 3000, or 5000 meters). In some embodiments, the housing 151 of the subsea laboratory 150 may define a pressurized container configured to maintain a predetermined pressure within the subsea laboratory 150, such as atmospheric pressure or other predetermined range (e.g., about 100 kilopascals (kPa) to 100 megapascals (MPa), 100 kPa to 30 MPa, or 100 kPa to 10 MPa). Additionally or alternatively, in certain embodiments, the housing 151 of the subsea laboratory 150 may include heating or cooling sources that are controlled to maintain a predetermined temperature within the subsea laboratory 150, such as an ambient temperature (e.g., about 18-25 degrees Celsius) or other predetermined range (e.g., about −15 to 75, 0 to 40, or 10 to 30 degrees Celsius). Such embodiments may enable use of generally available, less robust sensors or components (e.g., processor 154, memory device 156, or the like) in the subsea laboratory 150. In some embodiments, some or all of the subsea laboratory 150 may be subject to the subsea water pressure and/or temperature, which may facilitate analysis of the hydraulic fluid at conditions similar to operating conditions (e.g., at a pressure and/or temperature within 5, 10, 15, or 20 percent of the pressure and/or temperature at the location from which the hydraulic fluid is extracted from the BOP stack assembly 26 and/or the conduit 34 extending along the riser 32).

As shown, the subsea laboratory 150 includes a controller 152 (e.g., electronic controller) having a processor 154 and a memory device 156. In the illustrated embodiment, the subsea laboratory 150 includes one or more sensors 158 and one or more fluid chambers 160. In some embodiments, the subsea laboratory 150 may include one or more sub-chambers 161 and/or one or more chemical storage chambers 163. The subsea laboratory 150 may include a communications interface, such as a transceiver 162, that may be configured to communicate with other components of the monitoring system 100.

In certain embodiments, the fluid chambers 160 are configured to receive hydraulic fluid, such as hydraulic fluid from various fluid conduits or chambers 165 of the BOP stack assembly 26 and/or from the conduits 34 that extend along the riser 32 between the platform 22 and the BOP stack assembly 26. In some embodiments, one or more conduits 164 extend from the fluid conduits or chambers 165 of the BOP stack assembly 26 and/or from the conduits 34 to the fluid chamber 160 of the subsea laboratory 150. The flow of hydraulic fluid through the conduits 164 to the fluid chambers 160 of the subsea laboratory 150 may be adjusted via any suitable flow control device. For example, in some embodiments, one or more valves 166 may be provided to adjust fluid flow through the conduits 164. The valves 166 may be located proximate to the BOP stack assembly 26 and/or the conduits 34, or the valves 166 may be located within the subsea laboratory 150. When the valve 166 is in an open position, fluid may flow to the subsea laboratory 150 via the respective conduit 164. When the valve 166 is in a closed position, fluid may be blocked from flowing to the subsea laboratory 150 via the respective conduit 164.

The valves 166 may be controlled by the controller 152, or by any suitable electronic controller (e.g., a controller at the platform 22, a controller of the control units 50, internal or local controller, or the like). In some embodiments, the valves 166 may be controlled to open and close periodically (e.g., approximately every 1, 5, 10, 30, 60, or more minutes) to provide fluid from the various locations of the offshore system 20 to the subsea laboratory 150 for analysis. In some embodiments, the valves 166 may be controlled to open and close based on user inputs (e.g., input via a user interface at a base station). In some embodiments, the valves 166 may be controlled to open and close based on analysis or determined characteristics of the hydraulic fluid. For example, if one sample at a first location of the BOP stack assembly 26 includes a high number or particles (e.g., as determined by a particle counter sensor 158 in the subsea laboratory 150), a controller, such as the controller 152, may cause upstream valves 166 to open to enable analysis of the hydraulic fluid at upstream locations of the BOP stack assembly 26 and/or the conduit 34 to determine a source or entry point of the particles (e.g., a degrading or broken seal, leak point, or the like). By way of another example, while a hydraulic fluid sample obtained from a first location of the BOP stack assembly 26 (e.g., a location proximate to the exhaust and/or downstream location) is within tolerable limits (e.g., thresholds, which may be stored in a memory device, such as memory device 156), the controller, such as the controller 152, may maintain other valves 166 (e.g., upstream valves) in a closed position.

In certain embodiments, the subsea laboratory 150 may include any suitable number (e.g., 1, 2, 3, 4, 5, or more) of fluid chambers 160. In certain embodiments, each fluid chamber 160 may be coupled to a single conduit 164 that provides the hydraulic fluid from a single location of the BOP stack assembly 26 or the conduit 34. In some such cases, the subsea laboratory 150 may receive and/or analyze hydraulic fluid from various locations simultaneously. In some embodiments, each fluid chamber 160 may be coupled to multiple conduits 164. In some such cases, the subsea laboratory 150 may receive and/or analyze hydraulic fluid from various locations sequentially. For example, hydraulic fluid from a first location along the conduit 34 may be received in the fluid chamber 160, analyzed (e.g., via sensors 158), and removed from the fluid chamber 160. Subsequently, hydraulic fluid from another location along the conduit 34 or within the BOP stack assembly 26 may be received in the fluid chamber 160, analyzed (e.g., via sensors 158), and removed from the fluid chamber 160.

As noted above, the subsea laboratory 150 may include one or more sensors 158 that are configured to be controlled by the controller 152 to monitor a characteristic of the hydraulic fluid. Accordingly, each fluid chamber 160 may be equipped with or accessible to one or more sensors 158. Any of a variety of sensors 158 may be used to collect data related to the hydraulic fluid. For example, the one or more sensors 158 may include optical sensors (e.g., fiber optic sensor, refractometer, etc.) configured to monitor wavelength shifts, refractive index, light absorption, and/or other parameters indicative of characteristics of the hydraulic fluid. The one or more sensors 158 may include a pH meter, a particle counter, a salinity meter, a chemical sensor, an ultrasonic sensor, a conductivity meter, a temperature sensor, a viscometer (e.g., viscosity meter), and/or any suitable sensor 158 configured to detect the pH, the mix concentrate ratio, the glycol concentration, the water hardness, particle information, salinity, formaldehyde, alkalinity, conductivity, microbial inhibitor concentration, temperature, viscosity, or any combination thereof of the hydraulic fluid.

The one or more sensors 158 may be used to directly monitor the hydraulic fluid while the hydraulic fluid is supported within the fluid chamber 160, or a portion of the hydraulic fluid may be removed from the fluid chamber 160 and directed to a separate sub-chamber 161 within the subsea laboratory 150 for testing by a particular sensor 158. For example, in some embodiments, a portion of the hydraulic fluid may be directed to a respective sub-chamber 161 for chemical analysis and/or titration (e.g., chemicals from the chemical storage chamber 163 may be added to the hydraulic fluid to provoke a reaction and/or to facilitate determination of characteristics of the hydraulic fluid, such as the presence or concentration of certain inorganic or organic compounds). In some embodiments, the controller 152 may be configured to control valves within the subsea laboratory 150 to direct the various fluid flows (e.g., the flow of hydraulic fluid between chambers, the flow of chemicals, etc.).

The controller 152 may control the one or more sensors 158 to operate simultaneously or sequentially. In some embodiments, certain types of sensors 158 may be used to monitor the hydraulic fluid from one location (e.g., from the conduit 34) and different types of sensors 158 may be used to monitor the hydraulic fluid from another location (e.g., from the BOP stack assembly 26). In certain embodiments, separate sensors 158 may be provided for each fluid chamber 160. In some embodiments, one or more sensors 158 may be shared by fluid chambers 160, thus limiting the number of sensors 158 provided in the subsea laboratory 150. Additionally or alternatively, in some embodiments, one or more sensors 158 may be directly coupled to the fluid conduits or chambers 165 of the BOP stack assembly 26 and/or the conduit 34 to facilitate monitoring the hydraulic fluid, and a signal from the one or more sensors 158 may be provided to the subsea laboratory 150 and/or the base station (e.g., via electrical cables, wireless communication, or the like). The signals from such sensors 158 may be processed via the techniques disclosed herein to determine characteristics of the hydraulic fluid. The signals from such sensors 158 may be aggregated with signals from the sensors 158 within the subsea laboratory 150 or other sources, for example. Additionally or alternatively, in some embodiments, a surface laboratory having some or all of the features of the subsea laboratory 150 (e.g., fluid chambers 160, sensors 158, etc.) may be provided above the sea surface 24, such as on the platform 22, to test the hydraulic fluid to obtain baseline data prior flowing the hydraulic fluid into the conduits 34 toward the BOP stack assembly 26.

In some embodiments, the controller 152 may be configured to process signals received from the one or more sensors 158 to determine a characteristic of the hydraulic fluid and/or to determine an appropriate output (e.g., to control a particular valve 166, to monitor additional characteristics of the hydraulic fluid using other sensors 158, to provide an indication of the characteristics to an operator, to suggest an action to an operator, to automatically add an additive to the hydraulic fluid, to automatically flush the hydraulic fluid through the offshore system 20, or the like). In some embodiments, the controller 152 may not further process the raw data obtained by the sensors 158, but rather the controller 152 may store the raw data (e.g., in the memory device 156) and/or facilitate communication of the data to another controller (e.g., a controller 168 of a base station 170) for further processing. Thus, the controller 168 may carry out some or all of the processing steps with respect to the signals obtained from the sensors 158.

It may be desirable to communicate information between the subsea laboratory 150, the BOP stack assembly 26, the base station 170 positioned on the platform 22 or positioned at another location remote from the subsea laboratory 150, and/or other components of the offshore system 20. In certain embodiments, the subsea laboratory 150 may communicate determined characteristics of the hydraulic fluid or provide various determined outputs (e.g., outputs 130) and/or the subsea laboratory 150 may communicate raw data or the signals obtained from the sensors 158 for further processing, for example.

In the illustrated embodiment, electrical wires 172 (e.g., umbilicals) extend between the subsea laboratory 150 and the base station 170. The electrical wires 172 may facilitate the exchange of information and/or control signals between the subsea laboratory 150 and the base station 170. For example, the electrical wires 172 may enable signals from the sensors 158 to be provided to the controller 168 of the base station 170 and/or may enable control signals based on user inputs provided via an input 174 of the user interface 175 of the base station 170 to be provided to the controller 152 of the subsea laboratory 150. The signals from the sensors 158 may enable the controller 168 to provide an output (e.g., the output 130), while the control signals may instruct the controller 152 to utilize certain sensors 158 to test the hydraulic fluid and/or to open certain valves 166, for example. In some embodiments, the electrical wires 172 may extend along the riser 32 or through a separate conduit. It should be understood that other portions of the offshore system 20 may be communicably coupled to one another. For example, in certain embodiments, electrical wires 172 may extend between the subsea laboratory 150 and the BOP stack assembly 26. In certain embodiments, the subsea laboratory 150 may communicate control signals to the control unit 50 of the BOP stack assembly 26 and/or the control unit 50 may communicate data (e.g., data from sensors 158) to the subsea laboratory 150.

Additionally or alternatively, in certain embodiments, the subsea laboratory 150 may be configured to communicate indirectly with the base station 170 via a remotely operated vehicle (ROV) 176. As shown, the subsea laboratory 150 includes the transceiver 162, which is configured to wirelessly communicate with a transceiver 180 of a remotely operated vehicle (ROV) 176. The ROV 176 may include a controller 182 (e.g., electronic controller) having a processor 184 and a memory device 186 configured to store information received from the subsea laboratory 150. The ROV 176 may be configured to physically move between the subsea laboratory 150 and the base station 170. Thus, the ROV 176 may receive information from the subsea laboratory 150 via transceivers 162, 180, store the information in its memory device 186, and move toward the sea surface 24 to transfer information obtained from the subsea laboratory 150 to the base station 170 via transceivers 180, 181. The ROV 176 may be coupled to an ROV support vessel 183, which may be provided at the platform 22, the base station 70, or other location above the sea surface 24. In certain embodiments, the ROV support vessel 183 may include a controller 185 having a processor 187 and a memory 189, as well as a transceiver 181, which may be configured to receive data from the ROV 176 and to communicate data to the base station 170. Although the ROV 176 is illustrated, it should be understood that an autonomously operated vehicle (AOV) may be utilized instead.

As noted above, in certain embodiments, the controller 168 (e.g., electronic controller having a processor 189 and a memory device 191) of the base station 170 may be configured to receive and/or to determine characteristics of the hydraulic fluid based on measurements made by the sensors 158. In certain embodiments, the controller 168 may be configured to determine and/or to provide an output (e.g., output 130) via a display 190 or a speaker 192 of the user interface 175. For example, the controller 168 may be configured to provide an indication (e.g., visual and/or audible indication) of a characteristic of the hydraulic fluid (e.g., the pH, the mix concentrate ratio, the glycol concentration, the water hardness, particle information, salinity, formaldehyde concentration, alkalinity, conductivity, microbial inhibitor concentration, temperature, viscosity, or any combination thereof) via the display 190 or the speaker 192. For example, the controller 168 may cause display of a bar graph of multiple characteristics at a particular time or in a particular hydraulic fluid sample, a bar graph of one characteristic across multiple samples obtained at different times or at different locations, or a line graph of one or more characteristics over time or over multiple samples obtained at different times on the display 190. In some embodiments, the controller 168 may be configured to provide a visual or audible alarm (e.g., colored display, beep, or the like) based on the one or more characteristics. In some embodiments, the controller 168 may be configured to provide a prompt (e.g., textual or spoken instruction), such as an estimate of the remaining life of a component and/or an instruction to flush the hydraulic fluid through the offshore system 20, to add water, certain chemicals, and/or additives (e.g., biocide) to the hydraulic fluid, or the like, based on the one or more characteristics. In certain embodiments, the controller 168 may be configured to output a control signal to a fluid mixing system (e.g., located on the platform 22) to automatically adjust a composition or characteristic of the hydraulic fluid (e.g., automatically control a valve to flow water, a chemical, and/or an additive, such as biocide, into the hydraulic fluid) and/or to flush the hydraulic fluid through the offshore system 20 (e.g., automatically control a valve to cause the hydraulic fluid to flush through the offshore system 20) based on the one or more characteristics.

In certain embodiments, a single subsea laboratory 150 may be utilized as part of multiple offshore systems 20. For example, a single subsea laboratory 150 may be used to monitor hydraulic fluid from two or more different BOP stack assemblies 26 and corresponding conduits 34. In some such cases, the subsea laboratory 150 may simultaneously or sequentially receive and/or monitor hydraulic fluid from the multiple different BOP stack assemblies 26 and/or corresponding conduits 34. In some such cases, the subsea laboratory 150 may be movable (e.g., configured to be physically moved from one location to monitor a first BOP stack assembly 26 and/or its corresponding conduits 34 to another location to monitor a second BOP stack assembly 26 and/or its corresponding conduits 34). The subsea laboratory 150 may be physically moved subsea (e.g., via an ROV or an AUV) or topside (e.g., manually or via cranes or the like). In certain embodiments, multiple subsea laboratories 150 (e.g., 2, 3, 4, 5 or more) may be provided for one or more BOP stack assemblies 26, and one or more base stations 170 may be configured to receive and/or to process information from the multiple subsea laboratories 150.

Figure 5:
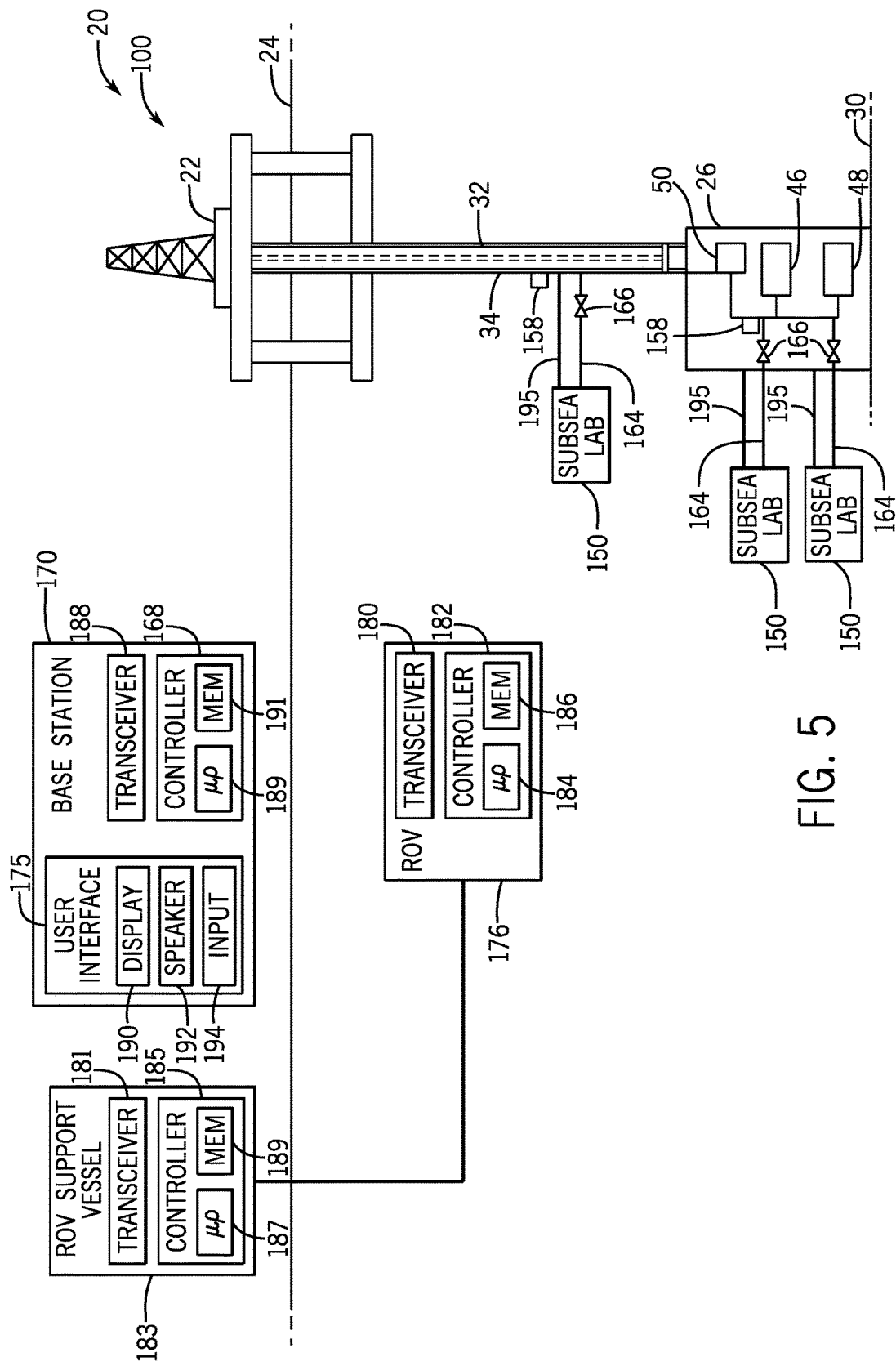
FIG. 5 is a block diagram of the monitoring system of FIG. 3 with multiple subsea laboratories coupled to subsea drilling and production equipment, in accordance with an embodiment of the present disclosure.

Although one subsea laboratory 150 is shown in FIG. 4, it should be understood that the components illustrated in the subsea laboratory 150 may be distributed about the BOP stack assembly 26 and/or the conduit 34 (e.g., individual sensors 158 distributed about the BOP stack assembly 26 and/or the conduit 34 may provide signals to a controller remote from each of these individual sensors 158). Furthermore, in certain embodiments, multiple subsea laboratories 150 may used to monitor the hydraulic fluid in a single BOP stack assembly 26 and/or the conduit 34. For example, as shown in FIG. 5, multiple subsea laboratories 150 are positioned at various locations of the offshore system 20 and are positioned to receive hydraulic fluid from different portions of the BOP stack assembly 26 and the conduit 34 (e.g., upstream of the control units 50, between the control units 50 and the annular BOP 46 and/or the ram BOP 48, downstream of the annular BOP 46 and/or the ram BOP 48, or any other suitable location). As noted above, in certain embodiments, the housing 151 of each subsea laboratory 150 may be coupled (e.g., removably coupled, fixedly attached, or internally integrated) with the BOP stack assembly 26 and/or the conduit 34, such as via respective fasteners 195. In some embodiments, subsea laboratories 150 may be positioned along the conduit 34 (e.g., every 150, 300, 450, or 600 meters), for example. Each subsea laboratory 150 may include the same or different sensors 158, and each subsea laboratory 150 may include any of the features discussed above with respect to FIG. 4.

As noted above, components of the monitoring system 100 may be distributed about the BOP stack assembly 26 and/or the conduit 34 in any of a variety of arrangements. For example, in some embodiments, it may be desirable for the subsea laboratory 150 at certain locations to be a relatively small component (e.g., to facilitate fastening to other equipment, moving to other locations, etc.). Thus, certain subsea laboratories 150 may include only a subset of the sensors 158 (e.g., 1, 2, 3, 4, or 5 sensors 158) described above. For example, in some embodiments, a first subsea laboratory 150 at a first location may be configured to monitor a first type of characteristic of the hydraulic fluid (e.g., pH, acidity, etc.), and a second subsea laboratory 150 at a second location may be configured to monitor a second type of characteristic of the hydraulic fluid (e.g., particle count, etc.). Furthermore, the other components shown in FIG. 5 may have any of the features discussed above with respect to FIG. 4. Additionally or alternatively, in some embodiments, one or more sensors 158 may be directly coupled to a fluid-handling portion of the BOP stack assembly 26 and/or the conduit 34 to facilitate monitoring the hydraulic fluid, and a signal from the one or more sensors 158 may be provided to the controller 152 of a respective subsea laboratory 150.

Figure 6:
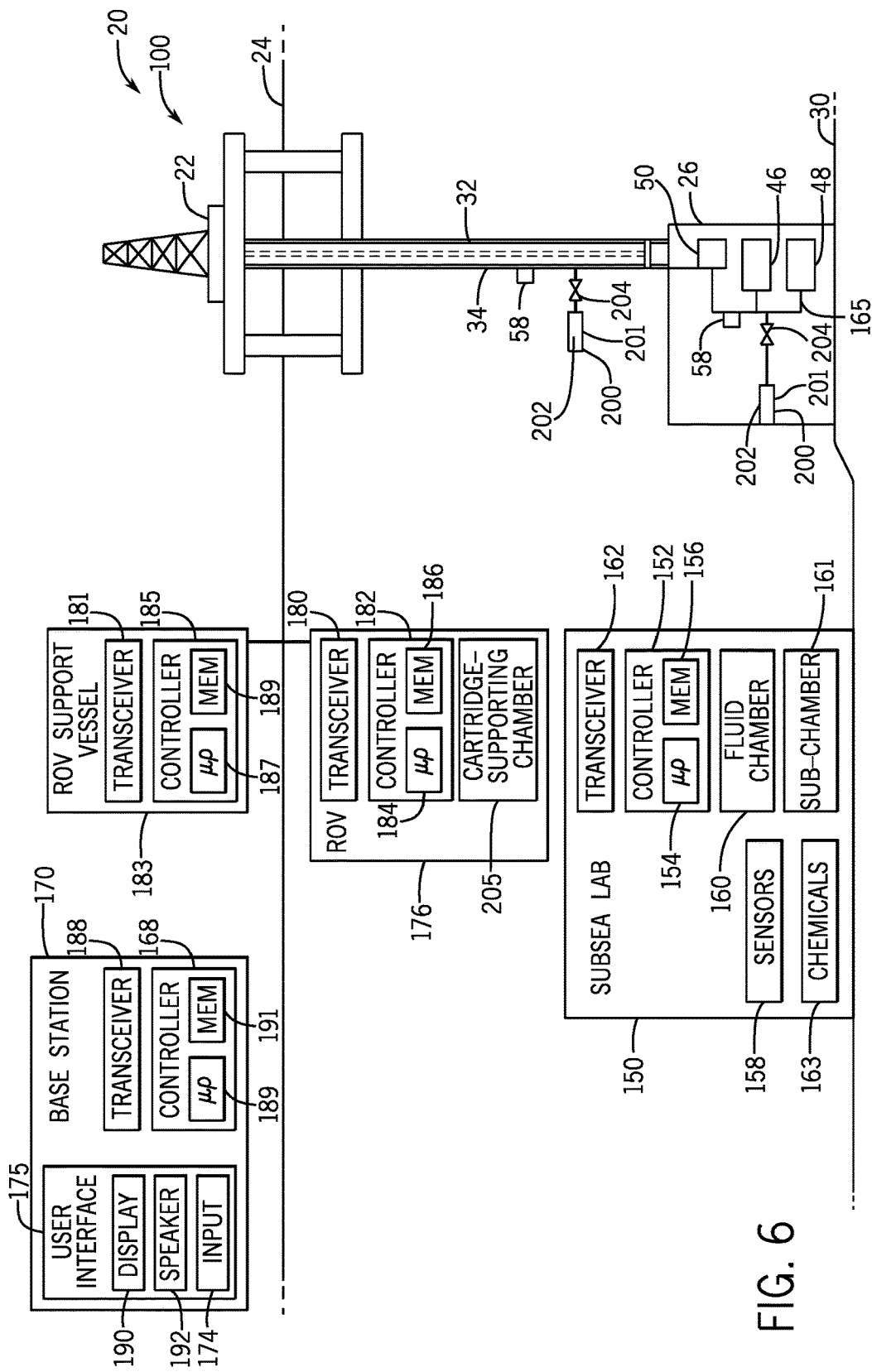
FIG. 6 is a block diagram of the monitoring system of FIG. 3 having movable cartridges to facilitate monitoring hydraulic fluid within subsea drilling and production equipment, in accordance with an embodiment of the present disclosure.

FIG. 6 illustrates another embodiment of the monitoring system 100 in which a cartridge 200 (e.g. capsule) is used to transport hydraulic fluid from the BOP stack assembly 26 and/or the conduits 34 to the subsea laboratory 150. The cartridge 200 may include a housing 201 supporting and/or defining one or more fluid chambers 202. The cartridge 200 may include a fluid inlet and/or a fluid outlet that enable fluid to flow into and from the fluid chambers 202 of the cartridge 200. The cartridge 200 may include mechanical connectors and/or electrical connectors that enable mechanical and/or electrical connection, respectively, with other components of the monitoring system 100 (e.g., the conduit 34, the BOP stack assembly 26, and/or the subsea lab 150). As shown, the cartridge 200 may be positioned to receive the hydraulic fluid from any suitable location of the BOP stack assembly 26 (e.g., upstream of the control units 50, between the control units 50 and the annular BOP 46 and/or the ram BOP 48, downstream of the annular BOP 46 and/or the ram BOP 48, or any other suitable location). A valve 204, which may be controlled by the control units 50, the controller 168, or the controller 152, may be provided to adjust a flow of the hydraulic fluid into the fluid chamber 202 of the cartridge 200. The valve 204 may have any of the characteristics discussed above with respect to the valve 166 of FIG. 4, for example.

The cartridge 200 may be configured to withstand subsea water pressure. In some embodiments, the fluid chamber 202 within the housing 201 may be configured to maintain the subsea water pressure and/or temperature, which may facilitate analysis of the hydraulic fluid at conditions similar to operating conditions (e.g., at a pressure and/or temperature within 5, 10, 15, or 20 percent of the pressure and/or temperature at the location from which the hydraulic fluid is extracted from the BOP stack assembly 26 and/or the conduit 34 extending along the riser 32). In some embodiments, the housing 201 may define a pressurized container configured to maintain a predetermined pressure within the cartridge 200, such as atmospheric pressure, subsea pressure, or other predetermined range (e.g., about 100 kilopascals (kPa) to 100 megapascals (MPa), 100 kPa to 30 MPa, or 100 kPa to 10 MPa), Additionally or alternatively, in certain embodiments, the housing 201 may be configured to maintain a predetermined temperature, such as an ambient temperature (e.g., about 18-25 degrees Celsius), subsea temperature, or other predetermined range (e.g., about −15 to 75, 0 to 40, or 10 to 30 degrees Celsius).

The cartridge 200 may be accessible to the ROV 176. In such embodiments, the ROV 176 may retrieve the cartridge 200 (e.g., via remotely controlled tools on the ROV 176) and transport the cartridge 200 within a cartridge-supporting chamber 205 to the subsea laboratory 150. The fluid chamber 160 of the subsea laboratory 150 may be configured to receive the cartridge 200 from the ROV 176 (e.g., through an opening in the housing 151 and via the remotely controlled tools on the ROV 176). The cartridge 200 may be configured to enable testing the hydraulic fluid using the sensors 158 within the fluid chamber 202. For example, the cartridge 200 may have transparent walls about the fluid chamber 202, include openings that enable the sensors 158 to access the hydraulic fluid within the fluid chamber 202, and/or openings that enable extraction of the hydraulic fluid for testing in various other chambers or sub-chambers 161. In some embodiments, some or all of the hydraulic fluid may be extracted from the cartridge 200 for testing in a separate fluid chamber or sub-chambers 161 of the subsea laboratory 150, as discussed above.

In some embodiments, multiple cartridges 200 may be stored at each desired location of the BOP stack assembly 26 (e.g., in a cartridge magazine). Additional cartridges 200 may be added (e.g., via the ROV 176) to the cartridge magazine to facilitate testing of the hydraulic fluid over time. The subsea laboratory 150 and the base station 170, and the components therein, may include any of the features discussed above with respect to FIG. 4. Furthermore, the testing may be carried out via any of the techniques disclosed above with respect to FIG. 4. As noted above, the various features disclosed herein may be combined in various manners. For example, in certain embodiments, the cartridges 200 may be utilized in conjunction with sensors 158 positioned on the BOP stack assembly 26 and/or the conduit 34 and/or the conduits 164 that are configured to flow the hydraulic fluid from the BOP stack assembly 26 and/or the conduit 34 to the fluid chamber 160, for example.

Figure 7:
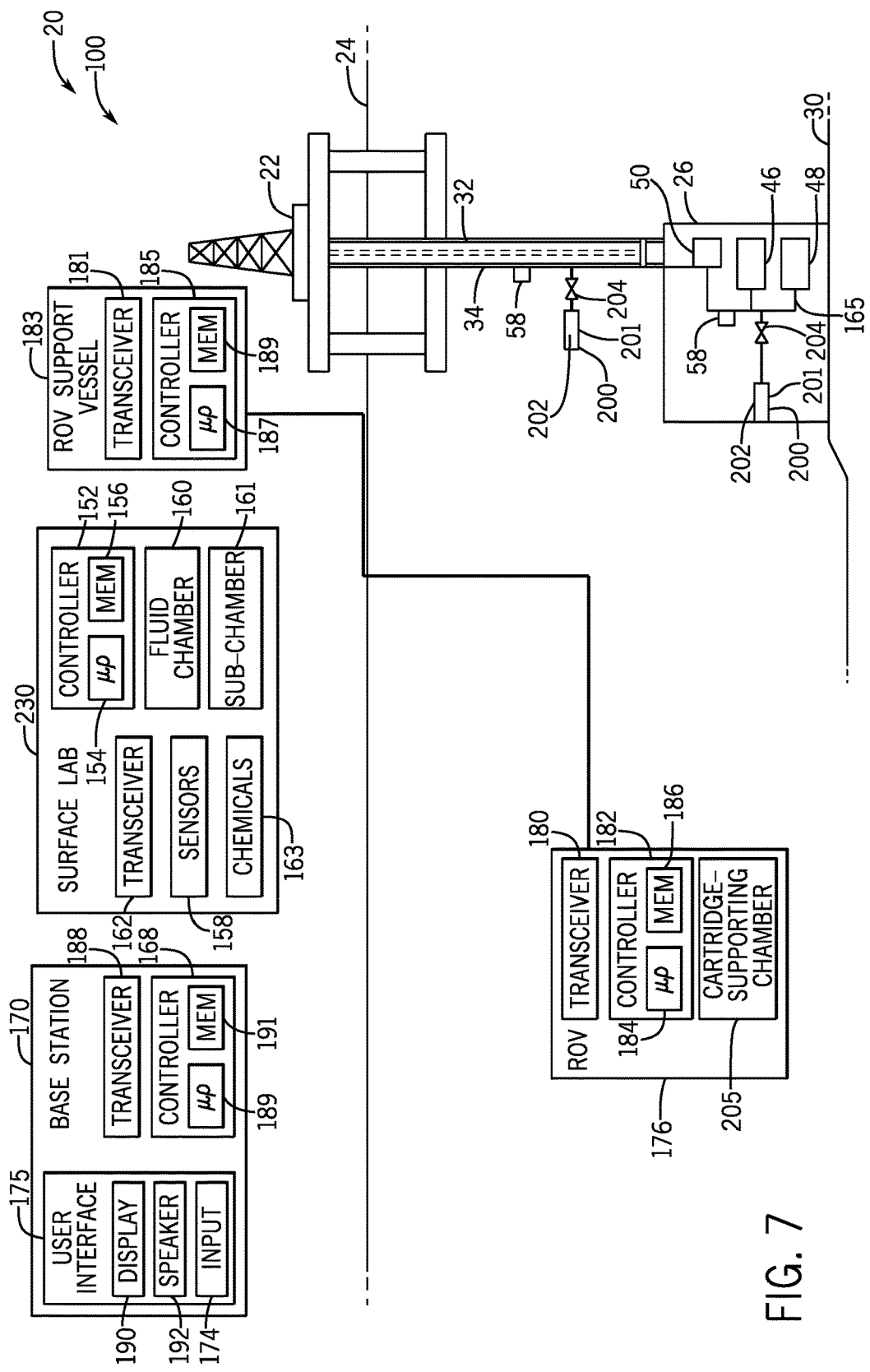
FIG. 7 is a block diagram of the monitoring system of FIG. 3 having movable cartridges and a surface laboratory to facilitate monitoring of hydraulic fluid within subsea drilling and production equipment, in accordance with an embodiment of the present disclosure.

FIG. 7 illustrates another embodiment of the monitoring system 100 in which an analysis laboratory 230 is located above the sea surface 24 (e.g., topside, such as on the platform 22). In certain embodiments, the analysis laboratory 230 may be configured to receive the hydraulic fluid via the cartridge 200. In some such cases, the cartridge 200 and/or the analysis laboratory 230 may be configured to maintain a temperature and/or a pressure within the fluid chamber during testing. Such a configuration may enable testing of the hydraulic fluid under conditions (e.g., pressure and temperature) similar to those present at the subsea location at which the hydraulic fluid was extracted from the BOP stack assembly 26 and/or conduit 34. Some or all of testing steps may be carried out manually (e.g., by an operator) in the analysis laboratory 230, and/or some or all of the testing steps may be carried out automatically (e.g., by a controller, such as the controller 158 described above) via the techniques discussed above with respect to the subsea laboratory 150. The analysis laboratory 230 may have any of the features discussed above with respect to the subsea laboratory 150 discussed in FIGS. 4-6.

Figure 8:
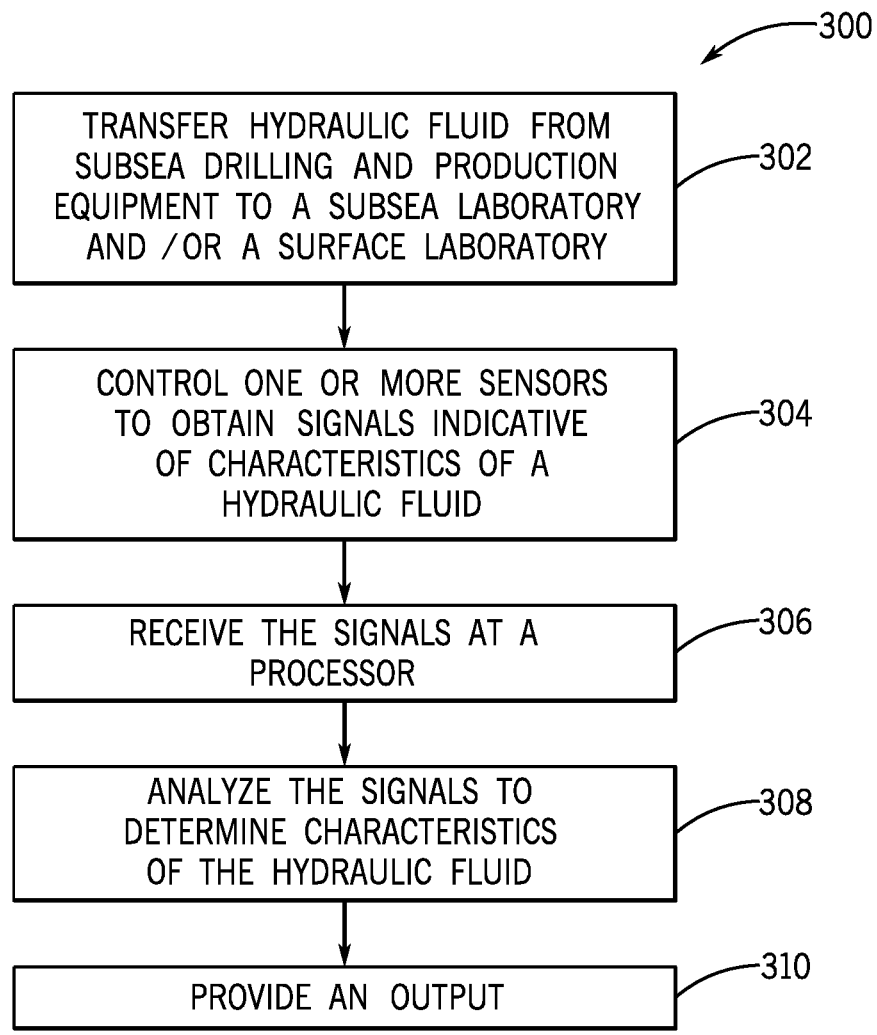
FIG. 8 is a flow diagram of a method for monitoring characteristics of hydraulic fluid.
Figure 9:
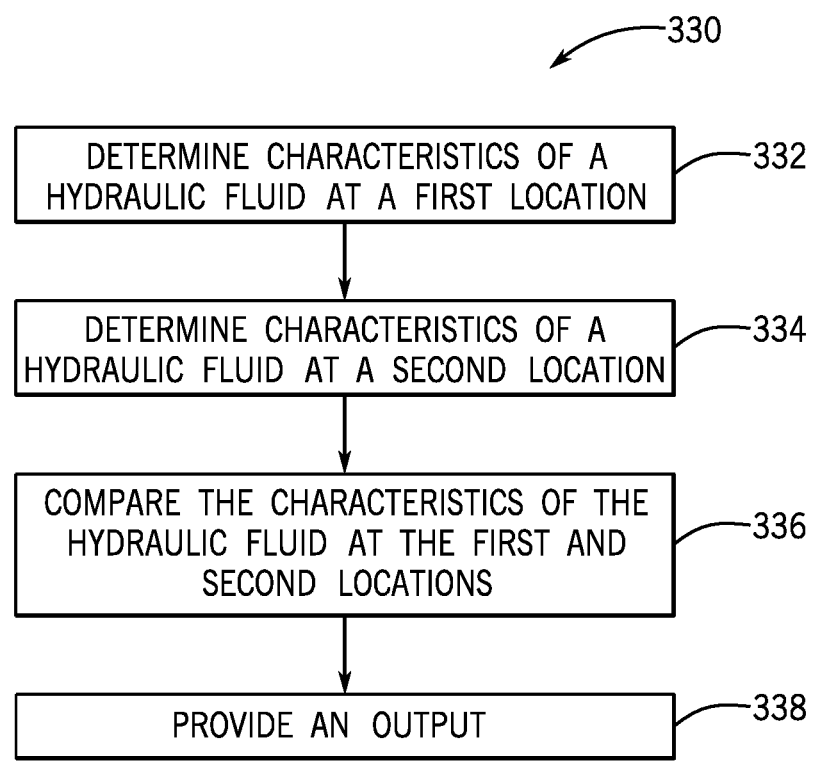
FIG. 9 is a flow diagram of another method for monitoring characteristics of hydraulic fluid.

FIGS. 8 and 9 are flow charts illustrating methods for monitoring hydraulic fluid of subsea drilling and production equipment, such as the hydraulic fluid within the BOP stack assembly 26 and/or the conduits 34, in accordance with the present disclosure. The methods include various steps represented by blocks. It should be noted that the methods provided herein, may be performed as an automated procedure by a system, such as the monitoring system 100. Although the flow charts illustrate the steps in a certain sequence, it should be understood that the steps may be performed in any suitable order and certain steps may be carried out simultaneously, where appropriate. Further, certain steps or portions of the methods may be omitted and other steps may be added. The steps or portions of the methods may be performed by separate devices. For example, a first portion of the methods may be performed by the processor 154, while a second portion of the methods may be performed by the processor 189. As noted above, the methods for monitoring the hydraulic fluid may be carried out periodically (e.g., based on instructions stored in a memory device, such as the memory device 156), in response to operator input (e.g., via the user interface 175), or the like.

FIG. 8 is a flow diagram of a method 300 for monitoring characteristics of hydraulic fluid. In step 302, hydraulic fluid may be transferred from the BOP stack assembly 26 and/or the corresponding conduit 34 extending along the riser 32 to the subsea laboratory and/or to the surface laboratory 230. The hydraulic fluid may be transferred in any of a variety of manners. For example, in some embodiments, valves 166 may be controlled to move from a closed position to an open position to enable the flow of the hydraulic fluid into conduits 164. As discussed above, the conduits 164 may extend from conduits or chambers 165 of the BOP stack assembly 26 and/or from the conduit 34 to a fluid chamber, such as the fluid chamber 160 of the subsea laboratory 150. In some embodiments, the hydraulic fluid may be transferred via one or more cartridges 200. In some such embodiments, the one or more cartridges 200 may be positioned at one or more locations about the BOP stack assembly 26 and/or along the conduit 34. The one or more cartridges 200 may be configured to collect samples of the hydraulic fluid from the BOP stack assembly 26 and/or along the conduit 34. For example, valves 204 may be opened to enable flow of the hydraulic fluid into respective fluid chambers 202 of the one or more cartridges 200. In some embodiments, multiple samples of hydraulic fluid at different times or from different locations of the BOP stack assembly 26 and/or the conduit 34 may be provided to multiple separate fluid chambers 202 that enable efficient sample collection and testing. As discussed above, in some embodiments, the one or more cartridges 200 may be accessed by and transported by the ROV 176 or other suitable machine to the subsea laboratory 150 and/or to the surface laboratory 230 for testing.

In step 304, one or more sensors, such as the one or more sensors 158, may be controlled or monitored (e.g., by the controller 152, the controller 168, or the control unit 50) to obtain signals indicative of characteristics of the hydraulic fluid extracted from the BOP stack assembly 26 and/or the conduit 34. As discussed above, the one or more sensors 158 may include optical sensors (e.g., fiber optic sensor, refractometer, etc.) configured to monitor wavelength shifts, refractive index, light absorption, and/or other parameters indicative of characteristics of the hydraulic fluid. The one or more sensors 158 may include a pH meter, a particle counter, a salinity meter, a chemical sensor, an ultrasonic sensor, a conductivity meter, a temperature sensor, a viscometer (e.g., viscosity meter), and/or any suitable sensor 158 configured to detect the pH, the mix concentrate ratio, the glycol concentration, the water hardness, particle information, salinity, formaldehyde, alkalinity, conductivity, microbial inhibitor concentration, temperature, viscosity, or any combination thereof of the hydraulic fluid. In some embodiments, some or all of the one or more sensors 158 may be positioned to test the hydraulic fluid within a fluid chamber 160 and/or a sub-chamber 161 of the subsea laboratory 150 (e.g., via openings in a wall of the fluid chamber 160, through a transparent wall of the fluid chamber 160, or the like). In certain embodiments, some or all of the sensors 158 may be positioned to test the hydraulic fluid in a surface laboratory, such as the analysis laboratory 230. In certain embodiments, some or all of the one or more sensors 158 may be positioned to directly test the hydraulic fluid in conduits or chambers 165 within the BOP stack assembly 26 and/or the conduits 34 (e.g., without extracting the hydraulic fluid).

In step 306, the signals generated by the one or more sensors 158 may be received at a controller, such as the controller 152 of the subsea laboratory 150 or the analysis laboratory 230. As noted above, in certain embodiments, the signals generated by the one or more sensors 158 may be provided to another controller for processing, such as the controller 168 of the remote base station 170.

In step 308, the signals are processed (e.g., by the controller 152 of the subsea laboratory 150 or the analysis laboratory 230, by the controller 168 of the remote base station 170, or other suitable controller) to determine characteristics of the hydraulic fluid. For example, the signals may be processed to determine the pH, the mix concentrate ratio, the glycol concentration, the water hardness, particle information, salinity, formaldehyde, alkalinity, conductivity, microbial inhibitor concentration, temperature, viscosity, or any combination thereof of the hydraulic fluid.

In step 310, a controller, such as the controller 152 of the subsea laboratory 150 or the analysis laboratory 230, by the controller 168 of the remote base station 170, or other suitable controller, may provide an output, such as the output 130. In certain embodiments, the output 130 may include an indication (e.g., visual and/or audible indication) of a characteristic of the hydraulic fluid (e.g., the pH, the mix concentrate ratio, the glycol concentration, the water hardness, particle information, salinity, formaldehyde concentration, alkalinity, conductivity, microbial inhibitor concentration, temperature, viscosity, or any combination thereof) via a display or a speaker. In some embodiments, the output 130 may include, via a display or a speaker, an alarm and/or a prompt, such as a suggestion that a component be replaced, that the hydraulic fluid be flushed through the offshore system 20, that water, certain chemicals, and/or additives (e.g., biocide) be added to the hydraulic fluid, or the like. In certain embodiments, the output 130 may include a control signal to automatically adjust a composition or characteristic of the hydraulic fluid (e.g., automatically control a valve to flow water, a chemical, and/or an additive, such as biocide, into the hydraulic fluid) and/or to flush the hydraulic fluid through the offshore system 20 based on the signals received and/or characteristics determined in steps 306 and 308. In this way, the monitoring system 100 is configured to provide information related to the hydraulic fluid of the BOP stack assembly 26 and/or carry out predictive maintenance techniques.

FIG. 9 is a flow diagram of another method 330 for monitoring characteristics of hydraulic fluid. In step 332, one or more characteristics of a hydraulic fluid from a first location of subsea drilling and production equipment, such as a first location within the BOP stack assembly 26 and/or the conduits 34, may be determined (e.g., via a controller, such as by the controller 152, the controller 168, or the control unit 50). To determine the one or more characteristics of the hydraulic fluid at the first location, the hydraulic fluid may be directly tested at the first location (e.g., via one or more sensors 158) or a sample of the hydraulic fluid may be extracted from the first location via any suitable technique, including the techniques disclosed herein (e.g., via the conduit 164, the cartridge 200, or the like). The one or more characteristics may be determined via the steps set forth in FIG. 8. In step 334, one or more characteristics of a hydraulic fluid from a second location of the subsea drilling and production equipment, such as the BOP stack assembly 26 and/or the conduits 34 may be determined. To determine the one or more characteristics, the hydraulic fluid may be directly tested at the second location (e.g., via one or more sensors 158) or a sample of the hydraulic fluid may be extracted from the second location via any suitable technique, including the techniques disclosed herein (e.g., via the conduit 164, the cartridge 200, or the like). In some embodiments, the hydraulic fluid may be sampled at more than two locations. Additionally or alternatively, the first location may be located topside (e.g., at the platform 22 or above the sea surface 24) to facilitate gathering baseline data or characteristics of the fluid prior to use within the subsea equipment.

In step 336, a controller (e.g., the controller 152 of the subsea laboratory 150 or the surface laboratory 230, by the controller 168 of the remote base station 170, or other suitable controller) may compare the characteristics of the hydraulic fluid at the first and second locations. In step 338, a controller, such as the controller 152 of the subsea laboratory 150 or the surface laboratory 230, the controller 168 of the remote base station 170, or other suitable controller, may provide an output, such as the output 130, in a manner similar to that discussed above with respect to step 310.

While the examples provided in FIGS. 2-8 relate to monitoring hydraulic fluid for the BOP stack assembly 26, it should be understood that the disclosed systems (e.g., the monitoring system 100) may be adapted for use with any of a variety of subsea equipment, such as fluid-handling processing and production equipment. It is envisaged that the holistic approach described herein can be iteratively applied to smaller and smaller increments of the system, starting with the system as the whole and moving to the top-level components, and then the components of the components, and so on.

The characteristics of the hydraulic fluid may be indicative of the health of the equipment and may be used for predictive maintenance, to estimate the remaining life of components, or the like. For example, the characteristics of the hydraulic fluid extracted from the subsea equipment (e.g., determined through the techniques discussed above), baseline data (e.g., collected at an earlier time or at the surface), known failure characteristic data (e.g., empirical data), and/or other types of data may be analyzed to determine the appropriate output or action, estimate the remaining life, or the like. Additionally or alternatively, a monitoring system, such as the monitoring system 100, may monitor the health and performance of various components, such as solenoid valves, in the BOP through other techniques. For example, the monitoring system 100 may be configured to monitor the performance of the solenoid valves via Bayesian Network analysis in which current performance is compared to the baseline performance of the valves (e.g., baseline data is stored in the monitoring system 100) and other, interdependent components or elements such as the BOP control fluid.

The AIM 10 discussed above with respect to FIG. 1 may additionally or alternatively be used in relation to the design and qualification of high-pressure/high-temperature (HPHT) production equipment, such as equipment rated for 20,000 psi or more. As one example, the AIM 10 can be employed to design a bi-metallic clad layer for structural capacity. That is, the structural capacity of the equipment, particularly for fatigue and crack growth, is viewed in conjunction with the clad layer, improving the process for determining resistance to fatigue crack growth and local strain damage as defined by ASME Sec. VIII, Div. 3. This is controlled by appropriate clad thickness, design analysis to assure the fatigue life and crack growth does not breach the clad layer, material properties testing of the clad weldment, increased non-destructive examination (NDE) inspection of the clad layer and component testing. In conjunction with some of the AIM concepts described herein, this process can be used to ensure the structural integrity for a bi-metallic clad system.

Crack growth in HPHT equipment can be characterized as 1) crack growth by fatigue; 2) stress corrosion cracking; 3) hydrogen assisted cracking; and 4) corrosion fatigue. One method for predicting crack growth is based on linear elastic fracture mechanics. The exemplary AIM method assumes a preexisting defect, where crack growth will start, at the highest stressed location oriented perpendicular to the maximum principal stress direction. The method employs the material properties of yield strength, flow stress, material toughness, and cyclic fatigue crack growth da/dN vs. ΔK. For HPHT applications, environmental testing allows for the use of material properties J vs. Δa and da/dN vs. ΔK for potential crack growth evaluation.

In addition, the design of well wetted pressure containing components can be evaluated to demonstrate any surface breaking defect can be contained within the alloy 625 weldment directly exposed to the production fluid, such as oil or natural gas.

Other material properties can be employed as well. For example, material properties generated for F22, alloy 625 weldment, alloy 718 and alloy 825 defining the true stress-strain material curves can be used for analysis. These curves can be adjusted to the minimum design and yield strength. Bolting data for alloy 718 can be defined as linear elastic properties with input of modulus and Poisson's ratio, and need not be part of the collapse load, strain limit damage, or ratcheting assessment requirements, for example.

As one example, the pressure containing material can be ASTM A182, F22 with an internal clad layer of alloy 625 weldments or solid alloy 718. The materials properties, which may or may not include bolting, are inputted into the finite element analysis (FEA) model, with true stress-true strain data at room temperature and high temperatures of 450 degrees Fahrenheit. Changing the element types from structural to thermal facilitates the steady state heat transfer solution to be determined for the components and bolting. This temperature distribution is "read into" the load steps of the structure simulation to account for thermal strains in conjunction with pressure and mechanical loads.

While the aspects of the present disclosure may be susceptible to various modifications and alternative forms, specific embodiments have been shown by way of example in the drawings and have been described in detail herein. But it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A monitoring system, comprising:
   a subsea laboratory configured to be positioned and operated below a sea surface, comprising:
      a housing;
      a fluid chamber within the housing and configured to receive a hydraulic control fluid extracted from subsea drilling or production equipment;
      a first sensor within the housing and configured to generate a first signal indicative of a first chemical composition of or a presence of particles within the hydraulic control fluid;
   a second sensor positioned above the sea surface and configured to generate a second chemical composition of or a presence of particles within the hydraulic control fluid; and
   a controller comprising a processor, wherein the processor is configured to receive and to process the first signal and the second signal to determine the first chemical composition of or presence of particles within the hydraulic control fluid and the second chemical composition of or a presence of particles within the hydraulic control fluid, to determine an appropriate output based on a comparison between the first chemical composition of or presence of particles within the hydraulic control fluid and the second chemical composition of or presence of particles within the hydraulic control fluid, and to provide a control signal that causes an indication of the output via a user interface positioned above the sea surface, wherein the output comprises an indication of health of the subsea drilling or production equipment, an indication of an operating life of the subsea drilling or production equipment, or a combination thereof.

2. The monitoring system of claim 1, comprising:
   a fluid conduit extending from the subsea drilling or production equipment to the fluid chamber; and
   a valve configured to move between an open position to enable flow of the hydraulic control fluid through the fluid conduit toward the fluid chamber and a closed position to block flow of the hydraulic control fluid through the fluid conduit toward the fluid chamber.

3. The monitoring system of claim 1, wherein the subsea drilling or production equipment comprises a blowout preventer (BOP) stack assembly and the hydraulic control fluid comprises BOP control fluid configured to drive movement of at least one of an annular BOP or a ram BOP of the BOP stack assembly, wherein the housing is coupled to and physically contacts the BOP stack assembly.

4. The monitoring system of claim 1, wherein the controller is positioned within the housing of the subsea laboratory.

5. The monitoring system of claim 1, wherein the user interface is part of an external system separate from the monitoring system, and the external system is configured to receive multiple signals from multiple monitoring systems and to provide respective audible or visual indications related to the subsea drilling or production equipment based on the multiple signals.

6. The monitoring system of claim 1, comprising a remotely operated vehicle (ROV) comprising an ROV transceiver configured to communicatively couple to a laboratory transceiver of the subsea laboratory to receive the first signal indicative of the first chemical composition of or presence of particles within the hydraulic control fluid and to communicatively couple to a base station transceiver of a remote base station having the controller and positioned above the sea surface to provide the first signal to the controller.

7. The monitoring system of claim 1, wherein the first sensor and the second sensor comprise an optical sensor, a pH meter, a particle counter, a salinity meter, a chemical sensor, an ultrasonic sensor, a conductivity meter, a temperature sensor, a viscometer, or any combination thereof, and wherein the first sensor and the second sensor are configured to generate a signal indicative of a pH, a mix concentrate ratio, a glycol concentration, a water hardness, a particle size, a particle material, a particle concentration, a salinity, a formaldehyde, an alkalinity, a conductivity, a microbial inhibitor concentration, a temperature, a viscosity, or any combination thereof.

8. The monitoring system of claim 1, comprising:
a cartridge configured to be coupled to the subsea drilling and production equipment to receive the hydraulic control fluid from the subsea drilling and production equipment and to be coupled to the subsea laboratory to deposit the hydraulic control fluid from the subsea drilling and production equipment at the subsea laboratory, wherein the cartridge is configured to be transported between the subsea drilling and production equipment and the subsea laboratory by a remotely operated vehicle or an autonomously operated vehicle.

9. The monitoring system of claim 1, wherein the housing defines a pressurized container configured to maintain a pressure within the housing while the housing is positioned and operated below the sea surface.

10. The monitoring system of claim 1, wherein the output comprises the indication of the operating life of the subsea drilling or production equipment.

11. The monitoring system of claim 1, wherein the second sensor is supported by a platform of an offshore system configured to extract a mineral resource from below the sea surface.

12. The monitoring system of claim 1, wherein the controller is configured to determine the appropriate output based on trends in the first chemical composition of or presence of particles within the hydraulic control fluid and the second chemical composition of or presence of particles within the hydraulic control fluid over a predetermined amount of time.

13. A monitoring system, comprising:
a valve configured to enable a flow of hydraulic control fluid from a conduit that provides the hydraulic control fluid used to drive an annular blowout preventer (BOP) component or a ram BOP component of a BOP stack assembly to a fluid chamber positioned beneath a sea surface;
a plurality of sensors configured to test the hydraulic control fluid within the fluid chamber and to generate respective signals indicative of a chemical composition of or a presence of particles within the hydraulic control fluid within the fluid chamber; and
a controller comprising a processor and a memory, wherein the processor is configured to receive and to process the respective signals to determine the composition of or the presence of particles within the hydraulic control fluid, to determine an appropriate output based on the composition of or the presence of particles within the hydraulic control fluid, to provide a first control signal to adjust a composition or characteristic of the hydraulic control fluid based on the composition of or the presence of particles within the hydraulic control fluid, and to provide a second control signal that causes an indication of the output via a user interface of a remote base station positioned above the sea surface, wherein the output comprises an indication of health of the BOP stack assembly, an indication of an operating life of the BOP stack assembly, or a combination thereof.

14. The monitoring system of claim 13, wherein the fluid chamber and the controller are positioned within a housing of a subsea laboratory.

15. The monitoring system of claim 13, wherein the controller is positioned within the remote base station.

16. The monitoring system of claim 13, wherein the plurality of sensors are configured to generate respective signals indicative of a pH, a mix concentrate ratio, a glycol concentration, a water hardness, a particle size, a particle material, a particle concentration, a salinity, a formaldehyde, an alkalinity, a conductivity, a microbial inhibitor concentration, a temperature, a viscosity, or any combination thereof.

17. The monitoring system of claim 13, wherein the fluid chamber is positioned within a cartridge configured to be coupled to the BOP stack assembly, the plurality of sensors are positioned within a housing of a subsea laboratory positioned beneath the sea surface, and the cartridge is configured to be transported between the BOP stack assembly and the subsea laboratory by a remotely operated vehicle or an autonomously operated vehicle to enable the plurality of sensors to test the hydraulic control fluid within the fluid chamber.

18. The monitoring system of claim 13, wherein the output comprises the indication of the operating life of the BOP stack assembly.

19. The monitoring system of claim 13, wherein the first control signal is configured to adjust a concentration of biocide in the hydraulic control fluid.

20. The monitoring system of claim 13, wherein the first control signal is configured to flush the hydraulic control fluid through an offshore system when a concentration of formaldehyde in the hydraulic control fluid reaches a threshold concentration.

21. A method for monitoring a hydraulic control fluid extracted from subsea drilling or production equipment, the method comprising:
receiving a hydraulic control fluid extracted from a first location with respect to subsea drilling or production equipment at a fluid chamber defined within a housing of a subsea laboratory positioned beneath a sea surface;

receiving, at a processor, a first signal indicative of a first chemical composition of or presence of particles within the hydraulic control fluid within the fluid chamber from a sensor configured to test the hydraulic control fluid within the fluid chamber;

processing, using the processor, the first signal to determine the first chemical composition of or presence of particles within the hydraulic control fluid;

receiving the hydraulic control fluid extracted from a second location with respect to the subsea drilling or production equipment at the fluid chamber;

receiving, at the processor, a second signal indicative of a second chemical composition of or presence of particles within the hydraulic control fluid within the fluid chamber from the sensor;

processing, using the processor, the second signal to determine the second chemical composition of or presence of particles within the hydraulic control fluid;

determining, using the processor, an appropriate output based on a comparison of the first chemical composition of or presence of particles within the hydraulic control fluid and the second chemical composition of or presence of particles within the hydraulic control fluid, wherein the output comprises an indication of health of the subsea drilling or production equipment, an indication of an operating life of the subsea drilling or production equipment, or a combination thereof; and providing, using the processor, a control signal that causes an indication of the output via a user interface of a remote base station positioned above the sea surface.

22. The method of claim 21, wherein the subsea drilling or production equipment comprises a blowout preventer (BOP) stack assembly.

23. The method of claim 22, comprising, using the processor, providing a drive signal to control a valve to transfer the hydraulic control fluid from a conduit that provides the hydraulic control fluid used to drive an annular blowout preventer (BOP) component or a ram BOP component of a BOP stack assembly to the fluid chamber.

24. The method of claim 21, comprising:
obtaining, using the processor, baseline data indicative of chemical composition of or presence of particles within the hydraulic control fluid above the sea surface prior to flowing the hydraulic control fluid into the subsea drilling and production equipment;

comparing, using the processor, the baseline data to the first chemical composition of or presence of particles within the hydraulic control fluid, or the second chemical composition of or presence of particles within the hydraulic control fluid, or both; and determining the appropriate output based on the comparison.

25. The method of claim 21, wherein the output comprises the indication of the operating life of the subsea drilling or production equipment.

26. The method of claim 21, comprising determining, using the processor, a source or entry point of particles into the hydraulic control fluid based on the first signal, the first chemical composition of or presence of particles within the hydraulic control fluid, the second signal, the second chemical composition of or presence of particles within the hydraulic control fluid, or a combination thereof.

* * * * *